United States Patent [19]

Meloen et al.

[11] Patent Number: 5,484,592
[45] Date of Patent: Jan. 16, 1996

[54] PEPTIDE, IMMUNOGENIC COMPOSITION AND VACCINE OR MEDICINAL PREPARATION: A METHOD OF IMMUNISING A MAMMAL AGAINST LHRH, AND A METHOD OF IMPROVING THE MEAT QUALITY OF PIGS

[75] Inventors: Robert H. Meloen; Cornelis J. G. Wensing, both of Lelystad, Netherlands

[73] Assignee: Stitching Centraal Diergeneeskundig Instituut, Netherlands

[21] Appl. No.: 149,001

[22] Filed: Nov. 8, 1993

Related U.S. Application Data

[63] Continuation of Ser. No. 761,849, Sep. 17, 1991, abandoned.

[30] Foreign Application Priority Data

Mar. 23, 1989 [NL] Netherlands ............... 8900726

[51] Int. Cl.⁶ ............... A61K 39/385; A61K 38/09; C07K 7/23
[52] U.S. Cl. ............... 424/185.1; 424/192.1; 424/195.11; 424/198.1; 530/313
[58] Field of Search ............... 424/185.1, 192.1, 424/198.1, 195.11; 435/69.4, 69.7; 530/313

[56] References Cited

U.S. PATENT DOCUMENTS 4,608,251  8/1986  Mia ............... 424/85

FOREIGN PATENT DOCUMENTS 8805308  7/1988  WIPO ............... A61K 39/385
9102799  3/1991  WIPO ............... C12N 15/62

OTHER PUBLICATIONS

Posnett, D. N. et al. (1988) J. Biol. Chem 263:1719–1725.
Jacob, C. O. et al. (1985) Mol. Immunol. 22:1333–1339.
Morrison et al., "Computer–Aided Design and Physiological . . . ," FEBS Lett 214:65–70 (1987). Abst Only.

Primary Examiner—Michael P. Woodward
Attorney, Agent, or Firm—Cooper & Dunham

[57] ABSTRACT

A peptide suitable for a vaccine effective against Luteinizing Hormone Releasing Hormone (LHRH) is disclosed. The peptide has an LHRH tandem structure, i.e., a peptide comprising at least 2 LHRH sequences in tandem. The invention further provides vaccines and medicinal preparations including the composition and a method of immunizing a mammal against LHRH.

10 Claims, No Drawings

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
( A ) LENGTH: 10 amino acids
( B ) TYPE: amino acid
( D ) TOPOLOGY: unknown ( i i ) MOLECULE TYPE: peptide ( x i ) SEQUENCE DESCRIPTION: SEQ ID NO:1:

Glu His Trp Ser Tyr Gly Leu Arg Pro Gly
1               5                   10

( 2 ) INFORMATION FOR SEQ ID NO:2:

( i ) SEQUENCE CHARACTERISTICS:
( A ) LENGTH: 10 amino acids
( B ) TYPE: amino acid
( D ) TOPOLOGY: unknown ( i i ) MOLECULE TYPE: peptide ( x i ) SEQUENCE DESCRIPTION: SEQ ID NO:2:

Cys Lys Trp Ser Tyr Gly Leu Arg Pro Gly
1               5                   10

( 2 ) INFORMATION FOR SEQ ID NO:3:

( i ) SEQUENCE CHARACTERISTICS:
( A ) LENGTH: 5 amino acids (B) TYPE: amino acid
(D) TOPOLOGY: unknown (ii) MOLECULE TYPE: peptide (xi) SEQUENCE DESCRIPTION: SEQ ID NO:3:

Glu His Trp Ser Tyr
1               5

(2) INFORMATION FOR SEQ ID NO:4:

(i) SEQUENCE CHARACTERISTICS:
    (A) LENGTH: 6 amino acids
    (B) TYPE: amino acid
    (D) TOPOLOGY: unknown (ii) MOLECULE TYPE: peptide (xi) SEQUENCE DESCRIPTION: SEQ ID NO:4:

Glu His Trp Ser Tyr Gly
1               5

(2) INFORMATION FOR SEQ ID NO:5:

(i) SEQUENCE CHARACTERISTICS:
    (A) LENGTH: 7 amino acids
    (B) TYPE: amino acid
    (D) TOPOLOGY: unknown (ii) MOLECULE TYPE: peptide (xi) SEQUENCE DESCRIPTION: SEQ ID NO:5:

Glu His Trp Ser Tyr Gly Leu
1               5

(2) INFORMATION FOR SEQ ID NO:6:

(i) SEQUENCE CHARACTERISTICS:
    (A) LENGTH: 7 amino acids
    (B) TYPE: amino acid
    (D) TOPOLOGY: unknown (ii) MOLECULE TYPE: peptide (xi) SEQUENCE DESCRIPTION: SEQ ID NO:6:

His Trp Ser Tyr Gly Leu Arg
1               5

(2) INFORMATION FOR SEQ ID NO:7:

(i) SEQUENCE CHARACTERISTICS:
    (A) LENGTH: 6 amino acids
    (B) TYPE: amino acid
    (D) TOPOLOGY: unknown (ii) MOLECULE TYPE: peptide (xi) SEQUENCE DESCRIPTION: SEQ ID NO:7:

Trp Ser Tyr Gly Leu Arg
1               5

(2) INFORMATION FOR SEQ ID NO:8:

(i) SEQUENCE CHARACTERISTICS:
    (A) LENGTH: 7 amino acids
    (B) TYPE: amino acid
    (D) TOPOLOGY: unknown (ii) MOLECULE TYPE: peptide ( x i ) SEQUENCE DESCRIPTION: SEQ ID NO:8:

Ser Tyr Gly Leu Arg Pro Gly
1               5

( 2 ) INFORMATION FOR SEQ ID NO:9:

( i ) SEQUENCE CHARACTERISTICS:
        ( A ) LENGTH: 6 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:9:

Tyr Gly Leu Arg Pro Gly
1               5

( 2 ) INFORMATION FOR SEQ ID NO:10:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:10:

Glx His Trp Ser Tyr Gly Leu Arg Pro Gly Gln His Trp Ser Tyr Gly
1               5                   10                  15

Leu Arg Pro Gly
            20

( 2 ) INFORMATION FOR SEQ ID NO:11:

( i ) SEQUENCE CHARACTERISTICS:
        ( A ) LENGTH: 21 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:11:

Glu His Trp Ser Tyr Gly Leu Arg Pro Gly Gln His Trp Ser Tyr Gly
1               5                   10                  15

Leu Arg Pro Gly Cys
            20

( 2 ) INFORMATION FOR SEQ ID NO:12:

( i ) SEQUENCE CHARACTERISTICS:
        ( A ) LENGTH: 21 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:12:

Glu His Trp Ser Tyr Gly Leu Arg Pro Gly Gin His Trp Ser Tyr Gly
1               5                   10                  15

Leu Arg Pro Gly Cys
            20

( 2 ) INFORMATION FOR SEQ ID NO:13:

( i ) SEQUENCE CHARACTERISTICS:
        ( A ) LENGTH: 11 amino acids
        ( B ) TYPE: amino acid (D) TOPOLOGY: unknown (i i) MOLECULE TYPE: peptide (x i) SEQUENCE DESCRIPTION: SEQ ID NO:13:

```
Glu His Trp Ser Tyr Gly Leu Arg Pro Gly Cys
1               5                   10
```

(2) INFORMATION FOR SEQ ID NO:14:

(i) SEQUENCE CHARACTERISTICS:
      (A) LENGTH: 11 amino acids
      (B) TYPE: amino acid
      (D) TOPOLOGY: unknown (i i) MOLECULE TYPE: peptide (x i) SEQUENCE DESCRIPTION: SEQ ID NO:14:

```
Glu His Trp Ser Tyr Trp Leu Arg Pro Gly Cys
1               5                   10
```

PEPTIDE, IMMUNOGENIC COMPOSITION AND VACCINE OR MEDICINAL PREPARATION: A METHOD OF IMMUNISING A MAMMAL AGAINST LHRH, AND A METHOD OF IMPROVING THE MEAT QUALITY OF PIGS

This is a continuation of application Ser. No. 07/761,849, filed Sep. 17, 1991, now abandoned.

This invention relates to a peptide suitable for realising a vaccine effective against LHRH, the "Luteinising Hormone Releasing Hormone", also referred to as the "Gonadotrophin Releasing Hormone" (GnRH).

The invention further relates to immunogenic compositions and vaccine or medicinal preparations (vaccines and pharmaceuticals) based on such a peptide and to the use of such a vaccine or medicinal preparation in a method of immunising a mammal against LHRH and in a method of improving the meat quality of pigs.

The hormone LHRH is a small peptide being 10 amino acids in length (i.e. a decapeptide) and having an amino acid sequence according to the formula (with, as usual, the amino terminal amino acid to the left and the carboxy terminal amino acid to the right):

pGlu-His-Trp-Ser-Tyr-Gly-Leu-Arg-Pro-Gly-NH$_2$, (SEQ ID NO:1)

in which the amino acids are designated according to the three-letter code, or according to the formula: #E H W S Y G L R P G@, in which the amino acids are designated according to the one-letter code, #E is pyroglutamic acid and G@ is glycine amide.

It is known that the LHRH, if coupled to a carrier protein, can be used to vaccinate mammals. Such a vaccination can be carried out for different reasons which are all connected with the natural function of the LHRH. The LHRH formed in the hypothalamus regulates in the hypophysis the formation of the sex hormones LH (i.e. "Luteinising Hormone") and FSH ("Follicle Stimulating Hormone"). As is known, a drastic reduction of the amounts of LH and FSH in the blood results in that in the male animal the production of androgens and sperm in the testis are inhibited and that in the female animal the formation of progestagens and oestrogens and the follicle maturation in the ovary are inhibited. Such a reduction of the amounts of androgens, progestagens and oestrogens in the blood to a level comparable to the level obtainable by castration or ovariectomy can be realised by effective immunisation of the animal against LHRH. In veterinary medicine, 100% effective immunisation could be used for the sterilisation of, e.g., small domestic animals such as male and female cats, or for the treatment of aggressiveness in male dogs, instead of drastic surgeries such as castration and ovariectomy. Other conceivable objects of immunisation against LHRH are to prevent heat in dogs and restlessness in steer fattening. In human health care, immunisation against LHRH can be used in the treatment of prostate cancer and breast cancer and, if required, in the treatment of some forms of hypophyseal carcinoma.

Another use of a vaccine against LHRH is in the field of stock breeding, particularly the fattening of pigs for slaughter. The meat of male, sexually mature pigs ("boars") has a typical odour, the so-called "boar odour". In the sexually mature pig there are formed in the testes many steroids which are stored in the fat tissue. These steroids (C 19Δ16 steroids) are responsible for the unpleasant urine-like "boar odour" formed when the meat is heated (see Brooks et al, J. Anim. Sci. 62, 1279 (1986). Owing to this unpleasant odour, meat of male, sexually mature pigs is hardly, if at all, suitable for consumption. Because about 10% of the male slaughter pigs are already sexually mature before the slaughter time, this potential entails a great loss for the pig farming industry. In order to check this loss, all male pigs are castrated when they are young, without stunning. Apart from the animal unfriendly aspect of such a castration, castration also leads to growth inhibition and a final meat quality inferior to that of an intact animal (at least as long as that intact animal has not yet developed boar odour).

An animal friendly alternative, which, in addition, benefits the meat quality, consists in the immunisation of the young animal against LHRH, thereby reducing the LHRH concentration in the hypophysis of the young animal. This reduction of the LHRH concentration in the hypophysis leads to a reduction of the concentrations of biologically active LH and FSH in the blood, which in turn results in that the development of the testes in the growing animal is prevented or delayed and that fewer steroids are formed. By effective vaccination against LHRH, it can therefore be avoided that the undesirable boar odour develops in pigs before the slaughter date.

It actually turns out in practice that in male animals the development of the testes can be delayed or stopped by vaccination with LHRH coupled to a carrier protein. The results, however, are often variable when use is made of the known vaccine preparations, such as those based on LHRH itself or on an analogue thereof, such as [D-Trp$^6$] LHRH (see Chaffaux et al, Recueil de Médecine Vétérinaire 161, 133–145 (1985)). For instance, there may be vaccinated animals which hardly, if at all, react to the vaccination. In the case of use in male young pigs to prevent development of boar odour, it is required for a good vaccine that in all pigs the development of the testis is delayed to the extent that in no case (up to 35 weeks after birth) boar odour develops, not even in a very large pig population. The known vaccine preparations do not meet this requirement.

This also applies to the immunogenic LHRH vaccines described in U.S. Pat. No. 4,608,251. The vaccines proposed therein are based on a nona- or decapeptide having the formula (C) K W S Y G L R P G@, (SEQ ID NO:2) or on a dimer of the decapeptide which can be formed by coupling via the amino terminal cysteines and satisfies the formula

This dimer does not seem to be more efficient than the monomeric peptides.

The international patent application WO 88/05308 proposes LHRH vaccines based on partial peptides of the LHRH having a length of 5, 6 or 7 amino acids, particularly those peptides which comprise either the amino terminal pGlu or the carboxy terminal Gly-NH$_2$. Examples of such partial peptides are (given in the one-letter code) #E H W S Y, (SEQ ID NO:3) #E H W S Y G, (SEQ ID NO:4) #E H W S Y G L, (SEQ ID NO:5) H W S Y G L R, (SEQ ID NO:6) W S Y G L R, (SEQ ID NO:7) S Y G L R P G@, (SEQ ID NO:8) and Y G L R P G@(SEQ ID NO:9). However, the vaccines based on these partial peptides also show the drawback mentioned before.

Surprisingly, it has now been found that a better and particularly more reliable vaccine is obtained if it is based on a peptide having an LHRH tandem structure, i.e. a peptide comprising at least 2 LHRH sequences arranged one behind the other.

Consequently, the invention first resides in a peptide which is characterised in that it comprises at least 2 LHRH sequences in tandem.

According to the invention there is preferred a peptide which is characterised in that it comprises at least 2 LHRH sequences in tandem according to the general formula (with the amino terminal amino acid to the left and the carboxy terminal amino acid to the right)

(SEQ ID NO: 10)

$Z^1$—Glx—His—$Trp^1$—Ser—Tyr—Gly—Leu—Arg—

—Pro[—Gly—X—Gln—His—$Trp^2$—Ser—Tyr—Gly—

—Leu—Arg—Pro]$_n$—Gly—$Z^2$, in which amino acids are designated according to the three-letter code, $Trp^1$ and $Trp^2$ are tryptophan (Trp) or formylated tryptophan ($N_{(indole)}$-formyl-tryptophan), n is a number having a value of at least 1,
X is either a direct bond or a spacer group between the amino acids Gly and Gln,
$Z^1$-Glx is either pGlu (pyroglutamic acid) or Gln having attached thereto a tail comprising one or more additional amino acids, and
Gly-$Z^2$ is either Gly-$NH_2$ or Gly having attached thereto a tail comprising one or more additional amino acids.

In this general formula, X may be a direct bond between the amino acids glycine and glutamine, i.e. these amino acids are interconnected directly without an intermediate link (via the normal peptide bond). Although this is preferred indeed, the invention also comprises peptides in which the LHRH sequences are interconnected via spacers. The nature of the spacer group may greatly vary from one or more amino acids to a shorter or longer hydrocarbon chain and other compound groups or molecules.

In the above general formula, $Z^1$-Glx preferably stands for pGlu (pyroglutamic acid), but can also stand for Gln having attached thereto a tail comprising one or more additional amino acids, e.g., to be used for coupling of the peptide to a carrier protein.

In the above general formula, Gly-$Z^2$ stands for e.g., Gly-$NH_2$, or Gly having attached thereto a tail comprising one or more additional amino acids, e.g., to be used for coupling of the peptide to a carrier protein. Preferably, Gly-$Z^2$ stands for Gly-Cys-$NH_2$, the C terminal cysteine being added in connection with a possible coupling of the peptide to a carrier protein.

More in particular, there is preferred according to the invention a peptide which is characterised in that it comprises at least 2 LHRH sequences in tandem according to the general formula (with the amino terminal amino acid to the left and the carboxyterminal amino acid to the right)

(SEQ ID NO: 11)

pGlu—His—$Trp^1$—Ser—Tyr—Gly—Leu—Arg—Pro[—Gly—

—Gln—His—$Trp^2$—Ser—Tyr—Gly—Leu—Arg—Pro]$_n$—

—Gly—Cys—$NH_2$, in which amino acids are indicated according to the three-letter code, $Trp^1$ and $Trp^2$ are either Trp or N-formyl-Trp, and n is a number having a value of at least 1.

A concrete example of such a preferred peptide is the peptide which comprises 2 LHRH sequences in tandem according to the formula (with the amino terminal amino acid to the left and the carboxy terminal amino acid to the right)

(SEQ ID NO: 12)

pGlu—His—$Trp^1$—Ser—Tyr—Gly—Leu—Arg—Pro—Gly—

-continued

—Gln—His—$Trp^2$—Ser—Tyr—Gly—Leu—Arg—Pro—

—Gly—Cys—$NH_2$, in which amino acids are designated according to the three-letter code, and $Trp^1$ and $Trp^2$ are either Trp or N-formyl-Trp.

The invention further resides in a composition which is characterised in that it comprises a peptide according to the invention brought into an immunogenic form. As a skilled worker knows, there are different methods of bringing a substance which by itself is not immunogenic, into an immunogenic form. A first possibility is to couple a peptide according to the invention to a suitable carrier protein. For a chemical coupling the C or the N terminus can be suitably used. Those skilled in the art perfectly know what coupling methods and what carrier proteins are eligible. See in this connection, e.g., the above cited U.S. Pat. No. 4,608,251 and WO 88/05308. According to the invention there is preferred a composition which is characterised in that it comprises an immunogenic conjugate of a protein and a peptide according to the invention. Another possibility is to convert the peptide by crosslinking into some larger complex, or to express the peptide by means of recombinant DNA manipulations as part of a (larger) protein. The invention therefore also resides in a composition comprising an immunogenic complex or an immunogenic recombinant protein to which a peptide according to the invention belongs.

Of course, the invention also resides in a vaccine or medicinal preparation which is characterised in that it comprises such a composition according to the invention in combination with at least one immunoadjuvant. Suitable immunoadjuvants are known to those skilled in the art and comprise, e.g., CFA (Complete Freund's Adjuvants) and IFA (Incomplete Freund's Adjuvants).

The invention further provides a method of immunising a mammal against LHRH, which method is characterised in that said mammal is vaccinated with such a vaccine or medicinal preparation according to the invention. Reasons for such a vaccination have already been indicated above, such as the use in human medicine for the treatment of prostate cancer and breast cancer and of some forms of hypophyseal carcinoma, various uses in veterinary medicine and various used in stock-breeding. A special use is within the scope of a method of improving the meat quality of pigs, which is characterised in that said pigs are vaccinated with such a vaccine preparation according to the invention.

The invention will be explained in more detail with reference to the following practical example.

EXAMPLE

Three groups of male young pigs (5 animals per group) were vaccinated with an LHRH vaccine after birth (day 0). The vaccines consisted of a peptide coupled to the carrier protein KLH (Keyhole Limpet Hemocyanine) via a C terminal cysteine. This coupling was effected by means of MBS (the compound m-maleimidobenzoyl-N-hydroxy succinimide ester, see Geysen et al, PNAS 81, 3998–4002 (1984)).

The peptides used were:
group I: LHRH
formula #E H W S Y G L R P G C@ (SEQ ID NO:13)
group II: [D-$Trp^6$]LHRH
formula #E H W S Y [D-Trp] L R P G C@ (SEQ ID NO:14)

group III: tandem LHRH formula #E H W S Y G L R P G Q H W S Y G L R P G C@

The peptides were emulsified after coupling to KLH (1 mg peptide to 1 mg KLH) in 1 ml CFA (1 ml peptide-KLH solution in 1 ml CFA). The emulsion was injected intramuscularly on day 0, and also 8 weeks later. During the second vaccination IFA was used.

A control group (group IV) was only vaccinated with the carrier protein (KLH) and adjuvant.

On day 0, and 4, 8 and 12 weeks later, the size of the testes was measured. On 17-18 weeks the animals were slaughtered. On 12 weeks after the first vaccination the testerone content was measured in the serum of the pigs. On 131 days after the first vaccination the testis and epididymis weights and the seminal vesicle and bulbourethral weights of the pigs were determined.

The results of the four groups were as follows. After a vaccination with LHRH (group I) external measurement showed that three out of five animals had smaller testes than the controls (group IV). Of the three animals having smaller testes, two had testes that had decreased in size to the extent that they could no longer be measured externally.

Of the animals vaccinated with [D-Trp$^6$]LHRH (group II), the testes of two out of five animals were clearly smaller than in the control animals, and in one animal the testes were no longer measurable.

Of the five animals vaccinated with tandem LHRH (group III), all the testes were smaller than in the control animals, and in four animals the testes were no longer measurable.

The mean testosterone contents in the serum were respectively:

2.47 (1.21) pmol/ml (control group, 5 pigs)

1.89 (2.24) pmol/ml (group I, 5 pigs)

2.72 (2.23) pmol/ml (group II, 5 pigs)

0.51 (0.08) pmol/ml (group III, 5 pigs).

The mean testis and epididymis weights were respectively:

285 (50) g/55 (11) g (control group, 5 pigs)

110 (123) g/21 (17) g (group I, 5 pigs)

221 (88) g/42 (12) g (group II, 5 pigs)

25 (11) g/11 (2) g (group III, 4 pigs).

The mean seminal vesicle and bulbourethral weights were respectively:

135 (44) g/119 (24) g (control group, 5 pigs)

40 (80) g/37 (48) g (group I, 5 pigs)

137 (71) g/135 (52) g (group II, 4 pigs)

5 (3) g/15 (5) g (group III, 4 pigs).

The bracketed values are the standard deviations.

Since delayed growth or even regression of the testis can be directly correlated with the decline of the androgen-producing capacity of the pig and consequently with the development of the undesirable boar odour, the contemplated complete protection is realised in group III treated with a tandem LHRH vaccine according to the invention, while only a partial protection was observed in groups I and II taken for comparative purposes.

We claim:

1. An immunogenic conjugate comprising at least one peptide of the formula p-Glu-His-Trp$^1$-Ser-Tyr-Gly-Leu-Arg-Pro-Gly-Gln-His-Trp$^2$-Ser-Tyr-Gly-Leu-Arg-Pro-Gly-Cys, with the amino terminal amino acid residue to the left and the carboxy terminal amino acid residue to the right, wherein Trp$^1$ and Trp$^2$ are either Trp or N-formyl-Trp, coupled to a carrier protein.

2. The immunogenic conjugate of claim 1, wherein the carrier protein is KLH.

3. A vaccine comprising a conjugate as claimed in claim 1 and an adjuvant.

4. A vaccine comprising a conjugate as claimed in claim 2 and an adjuvant.

5. The vaccine of claim 4 wherein the adjuvant is complete Freund's adjuvant.

6. The vaccine of claim 5 wherein the adjuvant is complete Freund's adjuvant.

7. A method of immunising a mammalian domestic animal against Luteinizing Hormone Releasing Hormone, comprising vaccinating said animal with the vaccine of claim 3.

8. A method of immunising a mammalian domestic animal against Luteinizing Hormone Releasing Hormone, comprising vaccinating said animal with the vaccine of claim 5.

9. A method of improving the meat quality of boars, comprising vaccinating said boars with the vaccine of claim 3.

10. A method of improving the meat quality of boars, comprising vaccinating said boars with the vaccine of claim 5.

* * * * *